United States Patent
Meier et al.

(10) Patent No.: US 6,183,465 B1
(45) Date of Patent: Feb. 6, 2001

(54) ADAPTER FOR A FEEDING SYSTEM

(75) Inventors: Kevin C. Meier, St. Louis, MO (US); Glenn Fournie, Smithon, IL (US); Alan Ranford, St. Louis, MO (US); Christy Martin Cummins, Tullamore; Sean Morris, Kiltoom, both of (IE)

(73) Assignee: Sherwood Services, AG (CH)

( * ) Notice: Under 35 U.S.C. 154(b), the term of this patent shall be extended for 0 days.

(21) Appl. No.: 09/387,647

(22) Filed: Sep. 1, 1999

(51) Int. Cl.$^7$ ................................................ A61M 25/16
(52) U.S. Cl. ...................... 604/535; 604/534; 604/533; 604/905
(58) Field of Search ................................ 604/167, 243, 604/256, 533, 534, 535, 536, 905

(56) References Cited

U.S. PATENT DOCUMENTS

| | | |
|---|---|---|
| 4,567,999 | 2/1986 | Hjertman et al. . |
| 4,888,008 | 12/1989 | D'Alo et al. . |
| 5,041,105 | 8/1991 | D'Alo et al. . |
| 5,053,015 * | 10/1991 | Gross ..................................... 604/167 |
| 5,209,740 * | 5/1993 | Bryant et al. ........................ 604/243 |
| 5,215,538 * | 6/1993 | Larkin ................................... 604/249 |
| 5,226,898 * | 7/1993 | Gross .................................... 604/283 |
| 5,303,751 | 4/1994 | Slater et al. . |
| 5,456,676 * | 10/1995 | Nelson et al. ........................ 604/283 |
| 5,607,392 * | 3/1997 | Kanner ................................... 604/86 |
| 5,624,414 | 4/1997 | Boettger . |
| 5,782,808 | 7/1998 | Folden . |
| 5,830,195 * | 11/1998 | Peters et al. ......................... 604/283 |
| 5,976,115 * | 11/1999 | Parris et al. ......................... 604/283 |

* cited by examiner

Primary Examiner—John G. Weiss
Assistant Examiner—David J. Cho
(74) Attorney, Agent, or Firm—Greensfelder, Hemker & Gale, P.C.

(57) ABSTRACT

An adapter utilized to interconnect a fluid container and a tubing set having a retractable spike and a rolling seal diaphragm for establishing fluid flow communication between a nutrition container and an administration tubing set while maintaining a fluid-tight seal. The rolling seal diaphragm includes a rolling seal portion which sealingly engages the retractable spike which remains engaged with the spike while the spike is biased between an engaged position and a disengaged position.

9 Claims, 5 Drawing Sheets

ADAPTER FOR A FEEDING SYSTEM

BACKGROUND OF THE INVENTION

1. Field of the Invention

The present invention generally relates to an adapter for interconnecting a fluid container with an administrative tubing set, and more particularly to an adapter having a retractable spike for use with a feed assembly. More specifically, the present invention relates to an adapter having a retractable spike and a rolling seal diaphragm arrangement for establishing fluid flow communication between a fluid container and an administration tubing set while maintaining a fluid-tight seal therebetween.

2. Prior Art

Feeding systems are frequently used to provide nutrition through either enteral or parenteral access to a patient unable to take nutrition orally. As used herein, the term nutrition shall be interpreted to include nutrition, medication and hydration. These feeding systems typically comprise an administration tubing set attached to a source of nutrition at one end and some kind of tube arrangement at the other end for providing nutrition immediately to a patient. In enteral feeding, the nutrition is typically administered to the patient by accessing a digestive organ through use of a nasogastric or gastrostomy tube which terminates in the stomach or a nasojejunal or jujunostomy tube which terminates in the jejunum. In contrast, parenteral feeding typically includes feeding nutrition by injection into a vein. Feeding systems also include fluid containers, which hold nutritional fluid in liquid form and typically include an opening sealed with a flexible membrane to seal and isolate the contents from environmental contaminates.

Often fluid containers of the above-mentioned character are connected to the administration tubing set by an adapter. One such adapter typical of the prior art is disclosed in U.S. Pat. No. 4,567,999 to Hjertman et al. entitled "Self-adhesive Connecting Device." Hjertman discloses an adapter for providing a sealed liquid connection with the orifice of a fluid container formed from a flexible sheet material. The adapter includes a hollow chamber with an outside surface adapted to be adhered to the container wall and a sharp point that is encased therein which is operative to penetrate the wall of the container. A pressure sensitive adhesive is provided on the outer peripheral surface of the Hjertman adapter that is intended to attach the adapter to the container wall such that the hollow chamber is sealed from outside contaminates.

Although the device of Hjertman et al. effectively provides a sealed liquid connection with a container, such devices also have several inherent drawbacks. Because the device to Hjertman entirely encloses the sharp point within the chamber, the user of these devices would need to apply a sufficiently strong exterior force to the chamber in order to actuate the device. However, directly exerting an exterior force upon the chamber to actuate the device increases the possibility of rupturing the chamber and resulting in mechanical failure of the device. Moreover, inadvertent impacts upon the chamber during transportation and storage are also likely to result in premature rupturing of the chamber. Finally, properly adhered to the container, such devices can not be easily reused with other fluid containers.

Other connection devices have been suggested to further advance the art. For instance, U.S. Pat. No. 5,041,105 to D'Alo et al. entitled "Vented Spike Connection Component," which is assigned to the assignee of the present invention, discloses a connection component suitable for use with a feeding set which includes a fluid container having a cap with an orifice and external threading disposed about the cap. A foil, or other similar frangible material, seals off the orifice of the container from fluid flow and outside contaminants. The connection component includes internal threading which mates with the external threading of the cap and a projecting spike which is adapted to penetrate the foil seal and establish fluid flow as the connection component is attached to the fluid container and actuated.

Although the D'Alo et al. device substantially advances the art, such connection components could still be further improved upon. The device to D'Alo et al. relies solely on frictional engagement between the threaded portion of the housing body and the threaded portion of the cap to create and maintain a fluid-tight seal. The device to D'Alo et al. also operates to simultaneously pierce the container when the user connects the connection component, and thus the operator must interconnect the device at the precise moment when it is desired to establish fluid flow. In other words, the operator can not attach the D'Alo et al. device to the pre-filled container without instantaneously piercing the foil seal and establishing fluid flow which may be undesirable. The operator must delay attaching the device to the container until needed, or the operator must attach the device to the fluid container and immediately establish fluid flow when the foil seal is pierced by the device connection.

Therefore, one skilled in the art can best appreciate that several advances would still be desirable. It would be desirable to have a connection device that may be properly secured to the container, while allowing the operator to delay piercing the fluid container and establish fluid flow when needed. It would also be desirable to have a connection device which provides a leak-free seal at all times between the fluid container, the connection device, and the administration tubing set.

OBJECTS AND SUMMARY OF THE INVENTION

In brief summary, the present invention overcomes and substantially alleviates the deficiencies in the prior art by providing an adapter that provides a rolling seal diaphragm which provides a leak-free connection site. The adapter operates as a connector between a fluid container and an administration tubing set with the fluid container having a cap that has an orifice and an external threading disposed about the cap. A foil, or other frangible membrane, seals off the orifice of the container from fluid flow prior to use. The administration tubing set includes hollow tubing which interconnects a tube arrangement attached to a patient to the fluid container via the adapter of the present invention.

The adapter comprises a body member connected between a spike member and a locking collar. The body member includes a body portion having a generally cylindrical shape and an annular ring formed thereon with a plurality of protrusions which are longitudinally formed along the body member. A pair of leg portions axially extends from the body portion with retention tabs formed at the free end thereof for engaging the body member to the spike member. The adapter further comprises a hollow rolling seal diaphragm positioned within the body member for providing a leak-free seal within the adapter during operation.

The spike member is coupled to the body member and includes a spike body which is generally frusto-conical in shape with an opposed pair of slots formed longitudinally along the spike body which are sized and shaped to slidably receive a corresponding protrusion formed along the body portion. An axial spike to penetrate the seal of the fluid container outwardly extends from the spike body and includes a longitudinal slot formed therealong which terminates at an angularly skewed end. Two generally opposed openings are formed through the spike body and are sized and shaped to receive and securely retain a respective leg portion of the body member thereto. As a result, the spike member is slidably coupled with the body member. The spike member also includes a tube adapter at its proximal end which axially extends therefrom and is adapted to attach the adapter of the present invention to the administration tubing set.

The locking collar is coupled to the body member and has a hollow cylindrical shape forming a chamber with opposed openings. An annular groove is adjacent one of the openings and is sized and shaped to be engaged by the annular ring formed around the body member such that the locking collar is engaged to the body member but rotates freely thereabout. The locking collar also includes an internal threaded portion disposed within the chamber proximate the other opposed opening for mating engagement with the external threaded portion of the fluid container when the adapter is attached thereto.

One unique aspect of the present invention is that it includes a hollow rolling seal diaphragm member disposed at least partially within the body member. The hollow rolling seal diaphragm member defines a diaphragm body having opposed openings and with a rolling seal portion and flange formed proximate one of the openings. More particularly, the rolling seal portion includes an outer portion with an inner portion integrally joined thereto, and substantially coaxially aligned with, the outer portion. Proximate the other opening, the diaphragm body includes an outer stepped portion. Once properly aligned within the body member, the outer stepped portion is sealingly engaged between the body member and the locking collar, while the flange crowns the other opening of the body member. In addition, the inwardly stepped portion of the diaphragm is adapted to abut the shoulder portion of the spike.

In operation, the operator of the present invention may easily and securely connect the adapter between the nutrition container and the administration tube set by first threading the threaded portion of the locking collar onto the threaded portion of the cap while the spike is isolated within the locking collar from inadvertent contact which may result in contamination of the spike. It will be appreciated that, although the adapter is secured to the container, the spike does not simultaneously pierce and breach the foil that seals off the orifice of the fluid container. Once the locking collar is properly secured, the administration tubing set is connected to the patient's tube arrangement while the spike member is maintained in the disengaged position. The operator will then grasp the spike body between the thumb and forefinger and move the spike member axially forward relative to the body member so that the spike extends forward from the locking collar and is driven through the foil of the fluid container, thereby establishing fluid flow. After the foil has been breached and fluid flow established, the operator will then release the spike member which will then be biased back within the locking collar in the disengaged position by the diaphragm. During operation of the adapter, the rolling seal diaphragm maintains a fluid tight seal about the axial spike as the spike is moved longitudinally.

Accordingly, the primary object of the present invention is to provide an adapter which is capable of establishing fluid flow communication between a fluid container and an administration tube set while maintaining a fluid-tight seal.

A further object of the present invention is to provide a rolling seal diaphragm that maintains a fluid-tight seal around the axial spike during operation of the adapter.

Another object of the present invention is to provide a connection device that allows the container to be sealingly connected to the administration tube set without simultaneously piercing the flexible membrane.

Another further object of the present invention is to provide a retractable touch free spike.

These and other objects of the present invention are realized in the preferred embodiment of the present invention, described by way of example and not by way of limitation, which provides for an adapter having a retractable spike and rolling seal diaphragm for establishing leak-free fluid flow communication between a fluid container and an administration tubing set.

Additional objects, advantages and novel features of the invention will be set forth in the description which follows, and will become apparent to those skilled in the art upon examination of the following more detailed description and drawings in which like elements of the invention are similarly numbered throughout.

DETAILED DESCRIPTION OF THE INVENTION

Figure 1:
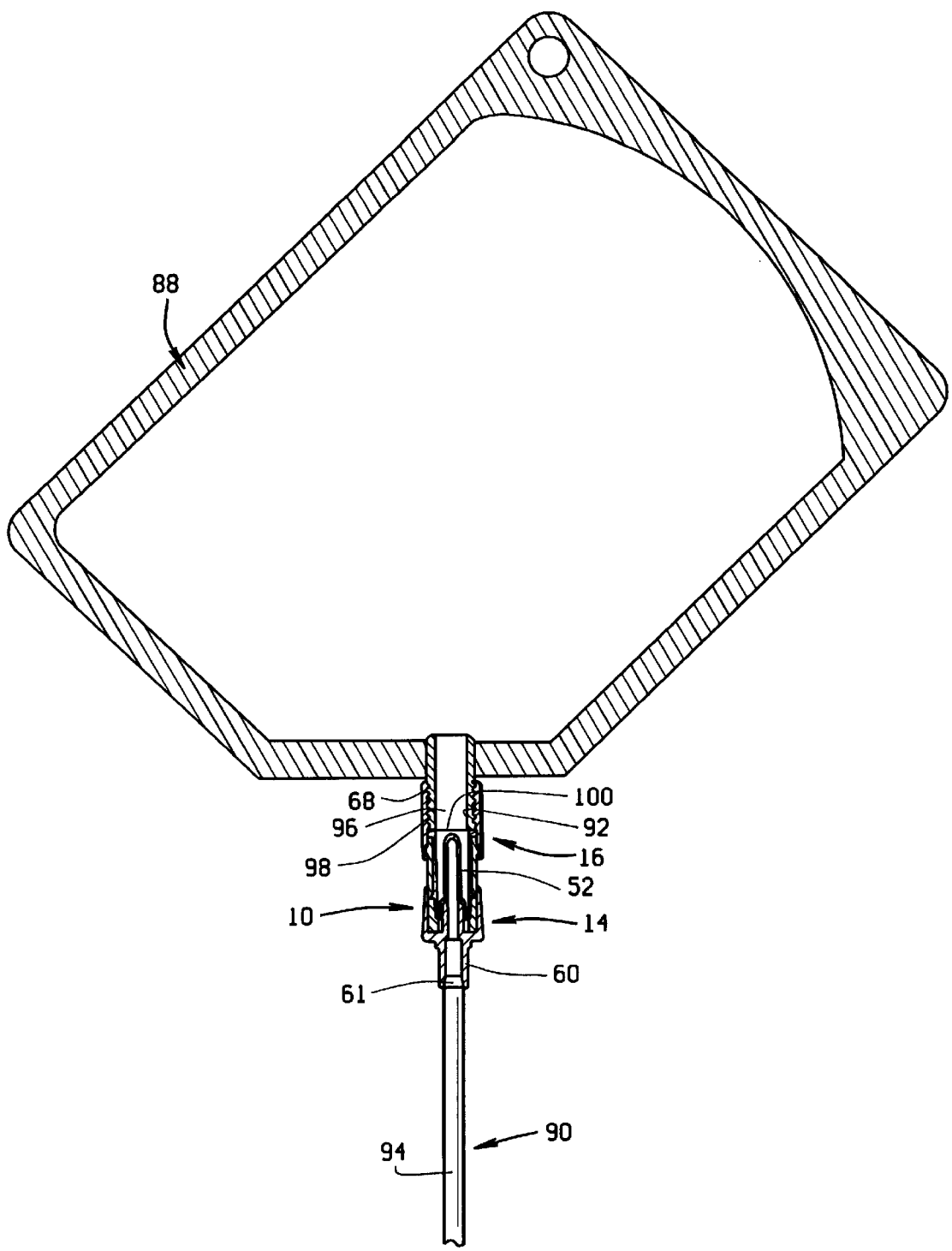
FIG. 1, is a cross-sectional view of a preferred embodiment of the adapter connected between a fluid container and an administration tubing set according to the present invention.
Figure 2:
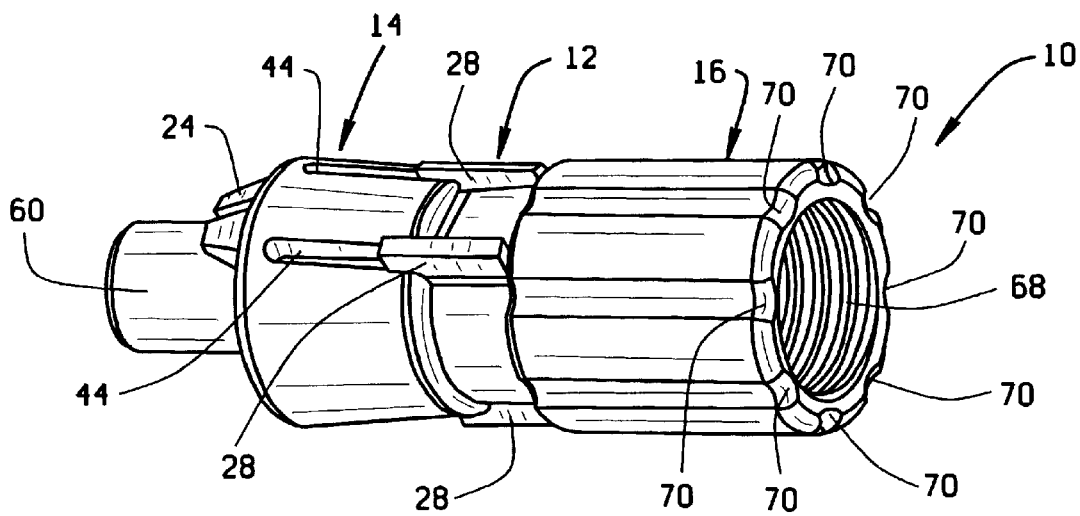
FIG. 2, is a perspective view of a preferred embodiment of the adapter according to the present invention.

Referring to the drawings, the preferred embodiment of the adapter for a feeding system of the present invention is illustrated and generally indicated as 10 in FIG. 2. As illustrated in FIG. 1, adapter 10 operates as a connector between a fluid container 88 and an administration tubing set 90 with the fluid container 88 including a cap 92 that has an orifice 96 and threading 98 disposed about the cap 92. A foil 100, or other frangible membrane, seals off the orifice 96 of container 88 from fluid flow. The administration tubing set 90 includes tubing 94 which interconnects a tube arrangement (not shown) which is connected to a patient to the fluid container 88 via the adapter 10 of the present invention. As shown in FIG. 2, the adapter 10 comprises a body member 12 slidably connected to a spike member 14 and rotatably connected to a locking collar 16. In addition, as seen in FIG. 3, adapter 10 further includes a rolling seal diaphragm 18 disposed within the body member 12.

Figure 3:
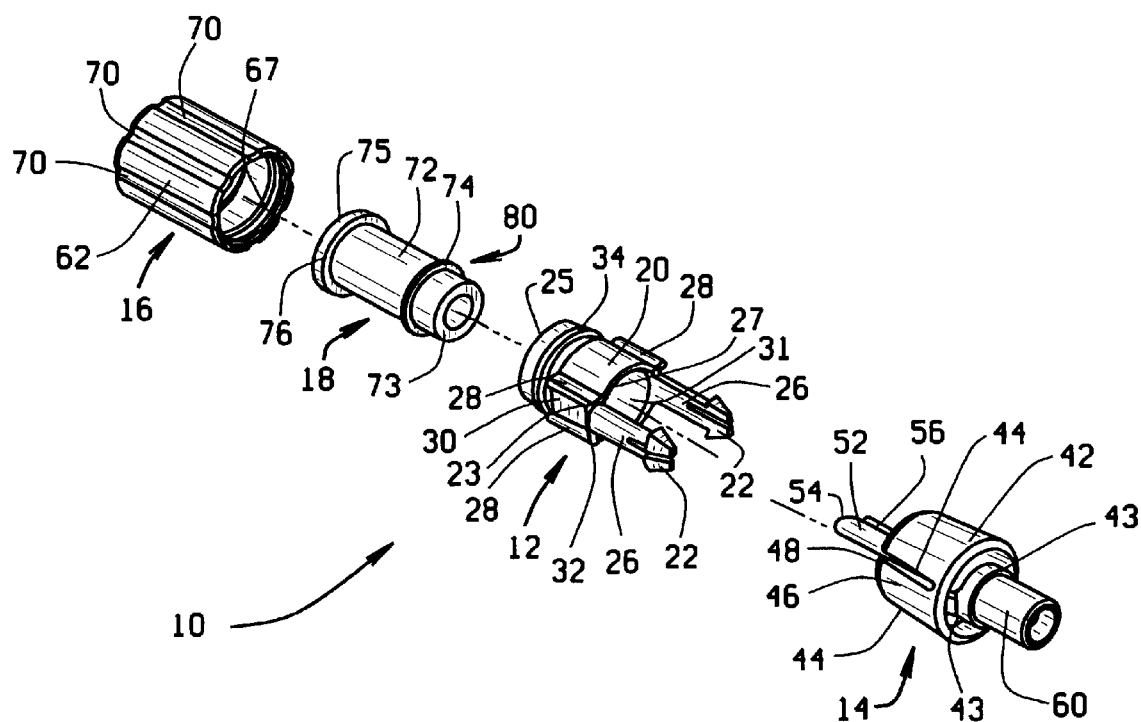
FIG. 3 is an exploded perspective view of the preferred embodiment of the adapter according to the present invention.

As best appreciated with reference to the exploded view shown in FIG. 3, the body member 12 comprises a hollow body portion 20 having opposed openings 25, 27 which form a channel 31 therebetween with a pair of laterally opposed leg portions 26 which extend axially proximate the opening 27. As shown, the preferred embodiment has a pair of leg portions 26. In the alternative, one skilled in the art can best appreciate that any suitable number of leg portions 26 may be utilized without departing from the teachings of the present invention. Each leg portion 26 includes a tab 22 formed at the free end of each leg portion 26. Preferably, tabs 22 are bifurcated along the free end thereof.

The body member 12 further includes an interior annular ridge 23 formed adjacent opening 27 and two pairs of opposed protrusions 28 longitudinally aligned and extending along the body portion 20. Formed between each pair of protrusions 28 is a beveled portion 30 defining a ledge 32. Further, body member 12 includes an exterior annular flange 34 formed proximate opening 25. Alternatively, it should be appreciated that any suitable number of protrusions 28 may be utilized without departing from the teachings of the present invention.

Figure 4A:
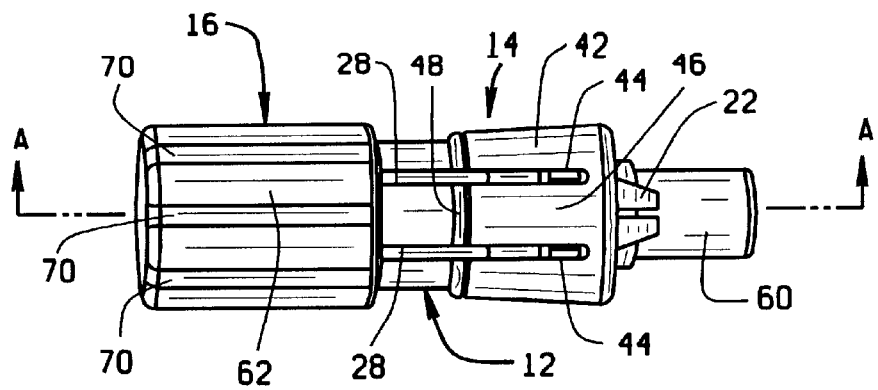
FIG. 4a is a side elevational view of the preferred embodiment of the adapter in an unactuated position according to the present invention.
Figure 4B:
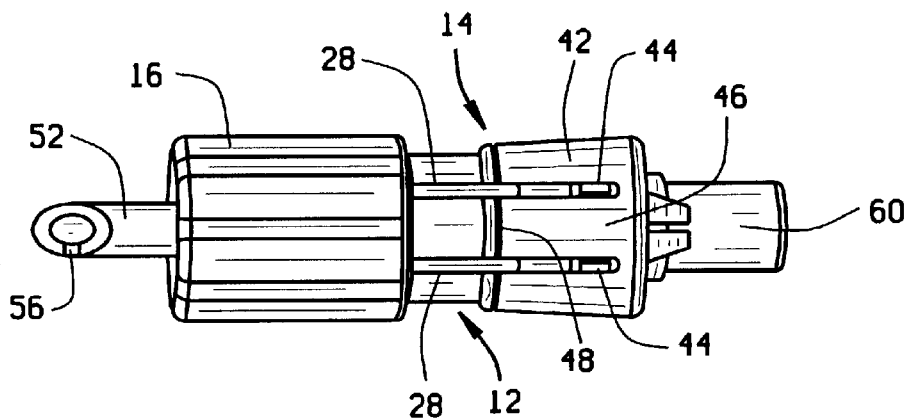
FIG. 4b is a side elevational view of an alternative embodiment of the adapter in an unactuated position according to the present invention.

As seen in FIGS. 3, 4a, and 4b, spike member 14 of adapter 10 comprises a spike body 42 defining two opposed pairs of longitudinal slots 44 which correspond to the two opposed pairs of protrusions 28 formed on body member 12. Each slot 44 is sized and shaped to slidably receive a corresponding protrusion 28 when the spike member 14 is in the actuated position, as shall be discussed in greater detail below. In addition, spike member 14 further includes two axial openings 43, as particularly shown in FIG. 3, which are sized and shaped to receive and retain a corresponding tab 22 of each leg portion 26. Alternatively, one skilled in the art can appreciate that any number of slots 44 and openings 43 may be utilized to interconnect the body member 12 to spike member 14 without departing from the teachings of the present invention.

Figure 6:
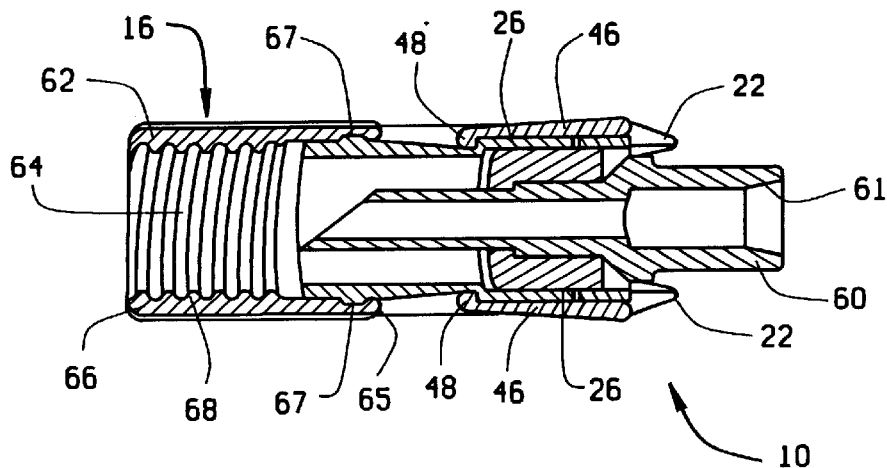
FIG. 6 is a cross-section of the preferred embodiment of the adapter along line A—A of FIG. 4a according to the present invention.

With reference to FIGS. 4a, 4b, and 6, each pair of slots 44 define a retention section 46 which includes a retention edge 48 formed at a distal or free end of each section 46. Each section 46 is positioned between a respective corresponding pair of protrusions 28 and is adapted to slide between each pair of protrusions 28 while traveling along the corresponding beveled surface 30 formed on the body member 12. During the aforementioned sliding action, the section 46 is prevented from separating from body member 12 due to the engagement between retention edge 48 of spike member 14 and the ledge 32 formed on body member 12 as well as the relative action of tab 22 with spike body 42, as shall be described with greater detail later.

Figure 7:
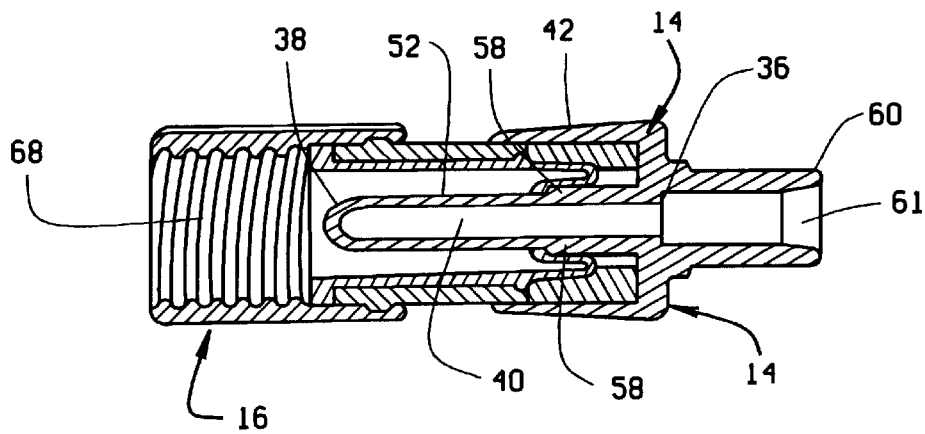
FIG. 7 is a cross-section of the preferred embodiment of the adapter along line B—B of FIG. 5 according to the present invention.

As best appreciated in FIG. 7, spike member 14 further includes an axial spike 52 outwardly extending from the spike body 42 defining opposed ends 36, 38 which form a channel 40 therebetween. With particular reference to FIG. 3, spike 52 includes a distal longitudinal slot 56 formed along a portion of spike 52 and that terminates at an angularly skewed end 54. Referring back to FIG. 7, circumferentially disposed about the spike 52 is a shoulder portion 58 which assists in forming a seal between the spike member 14 and diaphragm 18 as will be discussed in greater detail below. Spike body 42 further includes a proximal tube adapter 60 formed opposite spike 52 having an opening 61 aligned with spike 52 proximate end 36 and sized and shaped to be connected to administration tubing set 90, as illustrated in FIG. 1. Preferably, spike 52 is disposed entirely within the adapter 10 as illustrated in FIG. 4a. In an alternative embodiment shown in FIG. 4b, spike 52 extends beyond the collar 16 when adapter 10 is fully assembled.

Referring to FIG. 6, adapter 10 of the present invention also includes locking collar 16 comprising a body portion 62 with opposed openings 65, 66 forming a channel 64 therebetween. Channel 64 includes an annular groove 67 formed proximate opening 65 and a threaded portion 68 formed proximate opening 66. As seen in the preferred embodiment shown in FIG. 4a, longitudinal grooves 70 are formed along the body portion 62 of the locking collar 16 to enhance the ability of the operator to grasp the locking collar 16. However, one skilled in the art can best appreciate that a variety of other connective arrangements may be utilized without departing from the teachings of the present invention.

Figure 10:
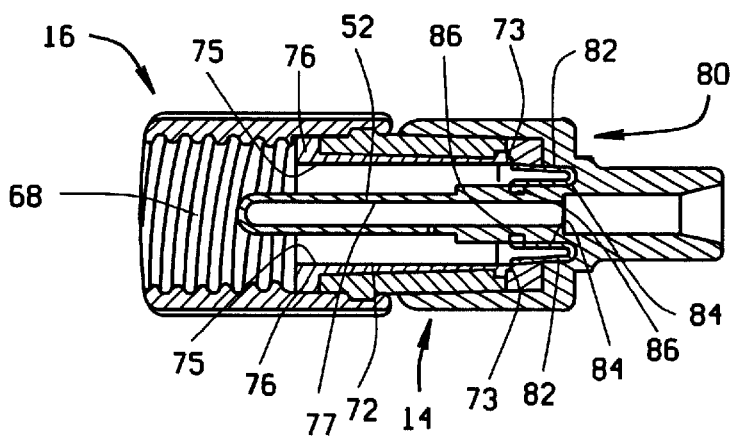
FIG. 10 is a cross-sectional view of the preferred embodiment of the adapter along line C—C of FIG. 8 according to the present invention.

As illustrated in FIG. 3, one unique aspect of adapter 10 is that it includes rolling seal diaphragm 18 which forms and maintains a fluid-tight seal during operation of adapter 10. With reference to FIGS. 3 and 10, diaphragm 18 comprises a body portion 72 which includes a pair of opposed openings 73, 75 with a channel 77 formed therebetween. Diaphragm 18 further comprises an annular flange 74 disposed proximate opening 73 and circumferentially disposed about the body portion 72, while an outer stepped portion 76 is formed proximate opening 75. The diaphragm 18 also is provided with a rolling seal portion 80 which is attachable to, or integral with, opening 73 and located adjacent flange 74 of body member 72. In particular, the rolling seal portion 80 includes an outer portion 82 and an inner portion 84 attached to, or integral with the outer portion 82 which is coaxially aligned and disposed within the outer portion 82. Both the inner portion 84 and outer portion 82 are generally cylindrical in shape. Attached to, or integral with, the inner portion 84 is an inwardly stepped portion 86 which abuts the shoulder portion 58 of the spike 52 and forms a rolling seal between the spike 52 and the inwardly stepped portion 86 of diaphragm 18 as the spike 52 is forced axially forward to the engaged position during operation of adapter 10. As the spike 52 is urged forward, the inward portion 84 of rolling seal portion 80 rolls along the spike 52 which is sealingly engaged therealong due to the engagement between the shoulder portion 58 of spike 52 and the inwardly stepped portion 86 of diaphragm 18. In response, the outer portion 82 of rolling seal portion 80 rolls inwardly allowing the inwardly stepped portion 86 to maintain a sealing engagement between moving spike 52 and diaphragm 18.

Figure 5:
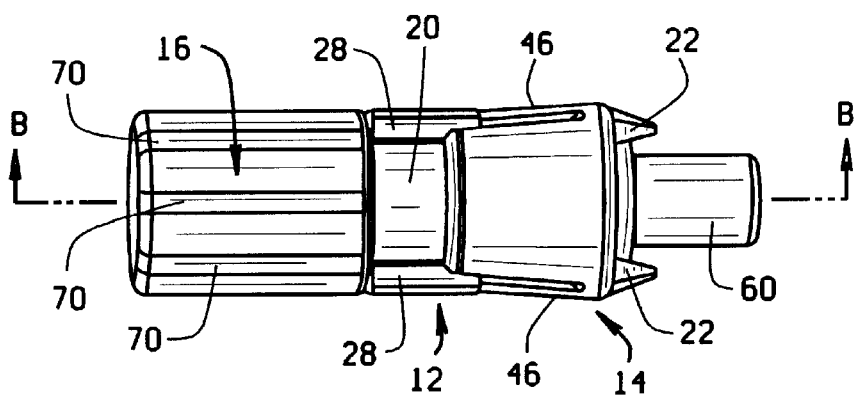
FIG. 5 is a top plan view of the preferred embodiment of the adapter in an unactuated position according to the present invention.
Figure 11:
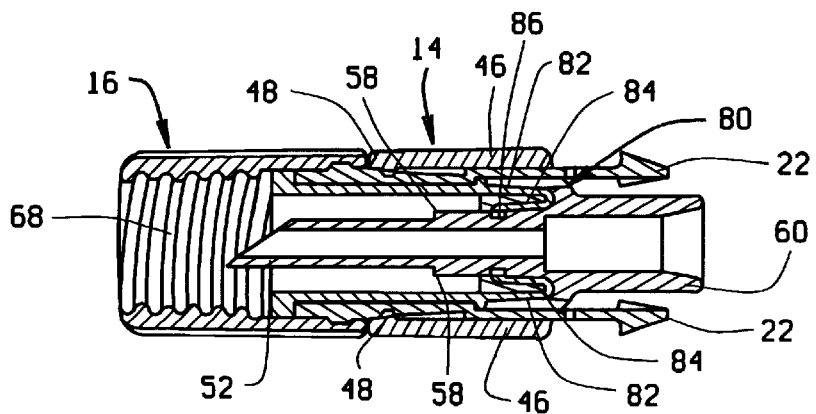
FIG. 11 is a cross-sectional view of the preferred embodiment of the adapter along line D—D of FIG. 9 according to the present invention.

With particular reference to FIG. 3, adapter 10 is assembled during manufacturing by first inserting diaphragm 18 within body member 12 by inserting diaphragm 18 through opening 25. Diaphragm 18 is then aligned within channel 31 such that the flange 74 crowns the ridge 23, while the outer stepped portion 76 abuts the opening 25 of body member 12 so that rolling seal portion 80 extends outwardly from body portion 20. Next, spike member 14 is connected to body member 12 and aligned such that each corresponding protrusion 28 is slidably received within each corresponding slot 44 of spike body 42. Spike member 14 is then axially depressed onto body member 12 until tabs 22 are passed through the corresponding openings 43 and retention edge 48 are disposed adjacent the beveled portion 30. The collar 16 is then engaged about the body member 12 so that annular flange 34 of body member 12 is engagingly received within the annular groove 66 of locking collar 16. Once assembled, spike member 14 may be biased between two positions: an actuated position, wherein spike member 14 abuts locking collar 16, as illustrated in FIGS. 10 and 11, and an unactuated position, wherein spike member 14 abuts tabs 22 of the body member 12, as seen in FIGS. 4a and 5.

Figure 8:
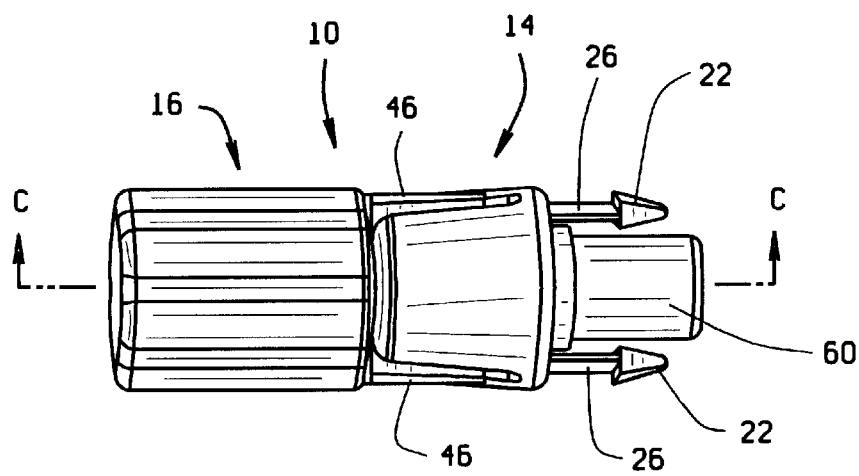
FIG. 8 is a top plan view of the preferred embodiment of the adapter in an actuated position according to the present invention.
Figure 9:
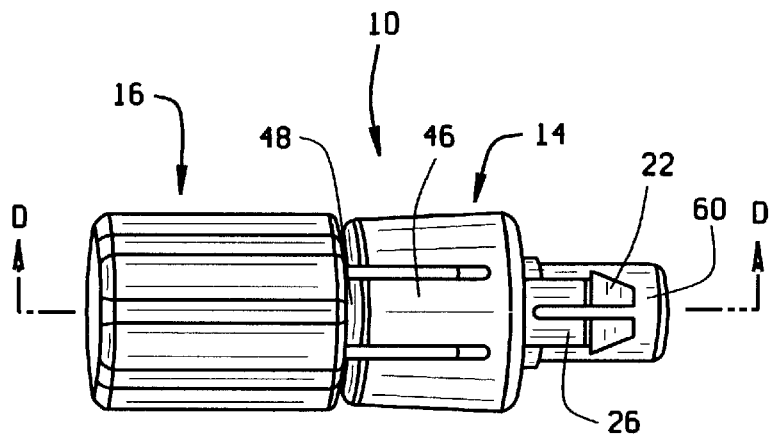
FIG. 9 is a side elevational view of the preferred embodiment of the adapter in an actuated position according to the present invention.

In operation, the adapter 10 of the present invention is uniquely configured to interconnect the fluid container 88 to the administration tubing set 90. As seen in FIG. 1, the adapter 10 is connected to the fluid container 88 by screwing the threaded portion 68 of the locking collar 16 onto the threaded portion 98 of the cap 92 while the spike 52 is isolated within the collar 16 to prevent undesirable contact and contamination of the axial spike 52. The operator then connects tube 94 which has been bonded to tube adapter 60 to the patient's tube arrangement. When it is desirable to actuate adapter 10 and establish fluid flow, the user will grasp spike member 14 preferably between the user's thumb and forefinger (not shown) and urge the spike member 14 forwardly as illustrated in FIGS. 8 and 9, through collar 16. With particular reference to FIGS. 10 and 11, the forward axial motion of spike 52 is restrained at one point by the abutment of retention edge 48 of spike member 14 with collar 16. As the spike member 14 is actuated by the user, the inward portion 84 of the rolling seal portion 80 rolls along the spike 52 which is sealingly engaged therealong due to the engagement between the shoulder portion 58 of spike 52 and the inwardly stepped portion 86 of diaphragm 18. In response, outer portion 82 of the rolling seal portion 80 rolls inwardly allowing the inwardly stepped portion 86 to maintain a sealing engagement between spike 52 and diaphragm 18. Once adapter 10 has been properly actuated, the operator will simply release spike member 14, as seen in FIGS. 4a and 5. Referring back to FIGS. 10 and 11, due to the inherent spring force of diaphragm 18, the spike member 14 will be automatically biased back towards the unactuated position with spike 52 isolated within collar 16 as the deformed rolling seal portion 80 unrolls back into its original undeformed orientation.

In the preferred embodiment, body member 12, the spike member 14, and the locking collar 16 are constructed from a substantially rigid medical-grade material, while diaphragm 18 is constructed from a substantially flexible elastic material. Most preferably, the body member 12, the spike member 14, and the locking collar 16 are constructed from a thermoplastic, such as ABS and the like, while diaphragm 18 is constructed from a thermoplastic, thermosetting rubber or other similar elastomeric material.

It should be understood from the foregoing that, while particular embodiments of the invention have been illustrated and described, various modifications can be made thereto without departing from the spirit and scope of the present invention. Therefore, it is not intended that the invention is limited by the specification; instead, the scope of the present invention is intended to be limited only by the appended claims.

What is claimed is:

1. An adapter comprising:
    a body member including a body portion having a generally cylindrical shape with an annular flange formed around said body portion, said body member further including at least one leg portion extending from the body member and at least one protrusion formed along said body portion;
    a spike member coupled with said body member including a spike body having a generally frusto-conical shape and defining at least one axial opening adapted to securely engage said at least one leg portion, said spike body further including at least one slot corresponding to said at least one protrusion, said spike member further defines a spike connected to said spike body;
    a collar member having a generally cylindrical shape forming an internal chamber with opposed openings, said collar member including an annular groove adjacent one of said openings, said groove being adapted to securely engage said annular flange; and
    a hollow diaphragm member disposed at least partially within said body member, said hollow diaphragm including a diaphragm body having opposed openings and a rolling seal portion proximate one of said openings.

2. An adapter as recited in claim 1, wherein said rolling seal portion comprises:
    an outer portion; and
    an inner portion connected to said outer portion.

3. An adapter as recited in claim 2, wherein said inner portion is co-axially aligned with said outer portion.

4. An adapter as recited in claim 3, wherein said rolling seal portion further comprises:
    an inner shoulder adapted to engage said spike.

5. An adapter as recited in 1, wherein said hollow diaphragm member further comprises:
    an outer shoulder disposed proximate other of said openings.

6. An adapter as recited in claim 5, wherein said channel further includes a threaded portion adjacent the other of said opposed openings.

7. An adapter comprising:
    a body member including a body portion having a generally cylindrical shape with an annular flange disposed on said body portion, said body member further including at least one leg portion extending from said body portion and at least one protrusion formed along said body portion;
    a spike member coupled with said body member, said spike member including a spike body having a generally frusto-conical shape and at least one axial opening adapted to securely engage said at least one leg portion, said spike being reciprocable between an engaged position and a disengaged position;
    a collar member having a generally cylindrical shape forming an internal chamber with opposed openings and an annular groove adjacent one of said opposed openings, said annular groove being adapted to securely engage said annular flange; and
    a hollow diaphragm member disposed at least partially within said body member and contacting said spike member such that said spike is springably urged towards said disengaged position.

8. An adapter as recited in claim 7, wherein said hollow diaphragm member is fabricated from an elastic material.

9. An adapter as recited in claim 7, wherein said body member, said spike member, said collar member, and said hollow diaphragm member are each constructed from a substantially liquid impermeable material.

* * * * *